United States Patent [19]

Böhner et al.

[11] 4,220,655
[45] Sep. 2, 1980

[54] PESTICIDAL 5-OXO-2,5 DIHYDROPYRROLE

[75] Inventors: Beat Böhner, Binningen; Marcus Baumann, Basel, both of Switzerland

[73] Assignee: Ciba-Geigy Corporation, Ardsley, N.Y.

[21] Appl. No.: 962,843

[22] Filed: Nov. 20, 1978

Related U.S. Application Data

[62] Division of Ser. No. 822,497, Aug. 8, 1977, Pat. No. 4,138,243.

[30] Foreign Application Priority Data

Aug. 12, 1976 [CH] Switzerland ............... 10309/76

[51] Int. Cl.² .................. A01N 9/22; C07D 207/24
[52] U.S. Cl. .............................. 424/274; 71/95;
260/326.41; 260/326.47; 260/326.5 S;
260/326.5 SF; 260/326.5 FL
[58] Field of Search ............... 260/326.45, 326.5 FL,
260/326.41, 326.47, 326.5 S, 326.5 SF; 71/95;
424/274

[56] References Cited

U.S. PATENT DOCUMENTS 3,673,211  6/1972  Winterfeldt ............... 260/326.5 FL
4,107,174  8/1978  Baumann et al. ........... 260/326 NS Primary Examiner—Dolph H. Torrence Attorney, Agent, or Firm—Harry Falber

[57] ABSTRACT

The present invention relates to novel 3,4-dimethyl-2-hydroxy-5-oxo-2,5-dihydropyrrole compounds substituted on the nitrogen atom, to processes for producing them, to their use in agriculture for combating animal and plant pests and also for regulating plant growth, and to compositions containing these novel pyrrole compounds.

The novel 3,4-dimethyl-2-hydroxy-5-oxo-2,5-dihydropyrrole compounds substituted on the nitrogen atom correspond to the formula

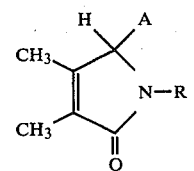

wherein
  A represents the hydroxyl group, a halogen atom or an O-acyl radical, and
  R represents an aryl radical, an aralkyl radical, or an heteroaromatic radical which has 5–6 ring members and which is bound by way of a carbon atom.

5 Claims, No Drawings

PESTICIDAL 5-OXO-2,5 DIHYDROPYRROLE

This is a division of application Ser. No. 822,497, filed on Aug. 8, 1977, now U.S. Pat. No. 4,138,243.

The present invention relates to novel 3,4-dimethyl-2-hydroxy-5-oxo-2,5-dihydropyrrole compounds substituted on the nitrogen atom, to processes for producing them, to their use in agriculture for combating animal and plant pests and also for regulating plant growth, and to compositions containing these novel pyrrole compounds.

The novel 3,4-dimethyl-2-hydroxy-5-oxo-2,5-dihydropyrrole compounds substituted on the nitrogen atom correspond to the formula

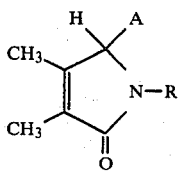 (I)

wherein
- A represents the hydroxyl group, a halogen atom or an O-acyl radical, and
- R represents an aryl radical, an aralkyl radical, or an heteroaromatic radical which has 5–6 ring members and which is bound by way of a carbon atom.

In the definition of the formula I, the aryl radical R is an unsubstituted phenyl or naphthyl radical or a mono- or poly-substituted phenyl or naphthyl radical, with the phenyl radical being preferred. Possible substituents of these rings are halogen atoms, alkyl, alkoxy or alkylthio groups, alkenyloxy, halogenoalkyl, halogenoalkenyl, alkynyl, alkynyloxy, cycloalkyl, phenyl, phenoxy or benzyloxy groups, the nitro, cyano, hydroxyl, mercapto or carboxyl radical, alkanoyl, alkoxycarbonyl, thiocarbonyl or benzoyl groups, carbamoyl radicals, alkylcarbamoyl radicals, carbamoyloxy groups, the amino group, mono-, dialkylamino or acylamino radicals, urea radicals, sulphinyl, sulphonyl or sulphamoyl radicals, halogenoalkylsulphamoyl radicals, the cyanato or thiocyanato group, with the alkyl groups containing in general 1 to 4 carbon atoms.

Preferred aralkyl radicals are benzyl and phenylethyl radicals radicals, the phenyl rings of which can be substituted as defined above.

The heterocyclic rings which apply in the case of R have 5 to 6 ring members, are aromatically unsaturated and are bound by way of a carbon atom to the 3,4-dimethyl-2-hydroxy-5-oxo-2,5-dihydro-pyrrole ring. Such a ring can be optionally substituted and can contain further hetero atoms. To be mentioned as examples are the imidazolyl, pyrazolyl, triazolyl, thiazolyl, isothiazolyl, oxadiazolyl, thiadiazolyl, oxazolyl, pyridyl, pyridazyl, pyrimidyl, pyrazyl and triazinyl rings.

If these rings are further substituted, they can contain for example halogen atoms, lower alkyl or alkoxy groups, or a substituent such as is possible for the aryl radical; or they can be condensed with further homo- or heterocyclic rings. The following may be mentioned as examples of condensed 5- or 6-membered hetero ring systems: benzimidazole, benzthiazole, benzoxazole, pterin, purine, quinoline, isoquinoline, naphthydrine, phthalazine, cinnoline, quinazoline and quinoxaline. These ring systems too can be substituted.

The O-acyl radical A is a preferably aliphatic carboxylic acid radical. It can be for example an alkyl carbonate or an alkyl thiocarbamate, such as a fatty acid radical. The fatty acid radical can be saturated or unsaturated and can contain up to 12 carbon atoms. The aliphatic radical of this acid can be substituted by halogen atoms, or interrupted by oxygen or by the —CO group. Also applicable are cycloaliphatic radicals such as cyclopropyl or cyclohexyl. The O-acyl radical can also be a carbamoyloxy radical optionally mono- or disubstituted on the nitrogen atom by $C_1$–$C_4$-alkyl, or the benzoyl radical, which can be substituted in the ring.

The compounds of the present invention are novel and are distinguished by a herbicidal, and for certain compounds also fungicidal, action, and they can be used for combating weeds or phytopathogenic fungi. Depending on the dosage, they act either as total or selective herbicides, and can be employed for controlling weeds in crops of cultivated plants. Other compounds of this invention are distinguished by having an acaricidal action, and are suitable for protecting cultivated crops or field fruits from infestation by spiders, mites and similar pests.

The compounds of the present invention are negligibly toxic to warm-blooded animals, and application of these compounds presents no problems. The amount applied is between 0.1 and 5 kg per hectare.

Some of the compounds according to the invention are likewise suitable for regulating plant growth. They inhibit for example the growth of mono- and dicotyledonous plants; furthermore, they promote the ripening and abscission of fruits.

Other compounds have a defoliating action and can be used for stripping and burning off unlignified parts of plants above the soil; for example for facilitating the harvesting of potatoes or cotton.

The novel 3,4-dimethyl-2-hydroxy-5-oxo-2,5-dihydropyrrole compounds of the formula I are produced by reduction of a dimethyl-maleic acid imide, substituted on the nitrogen atom, of the formula II

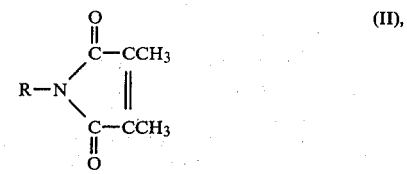 (II), wherein R has the meaning given under the formula I, with a hydrogenating agent.

The reduction is performed at a temperature of −20°–+80° C., in a solvent, by means of a reducing agent. Suitable reducing agents are sodium hydride, lithium aluminium hydride and other metal hydrides which generate hydrogen. Furthermore, catalytic hydrogenation can be performed.

If A is not to remain the hydroxyl group, this is esterified in a known manner with an acid or an acid halide. The reaction of the hydroxyl group to the halide is performed in a known manner by reaction with an acid halide such as thionyl chloride or thionyl bromide, or with another strong halogenating agent, e.g. phosphorus oxychloride and phosphorus oxybromide, or phosphorus pentachloride and phosphorus pentabromide, respectively. An O-acyl group A can be introduced into the 2-position of the pyrrole ring by esterifying, in a known manner, the hydroxyl group present in this position with a carboxylic acid derivative; or by reacting a halogen atom present there with a carboxylic acid derivative.

The compounds of the formula I can be used as such, or as salts isolated with strong organic or inorganic acids.

The solvents used can be lower alkanols, ethers or tetrahydrofuran and also water. The said reductions can be performed under normal pressure in customary apparatus.

Some of the dimethyl-maleic acid imides of the formula II are known compounds, the production of which is described in the German Offenlegungsschrift No. 2,233,889, in the French Patent Specification No. 2,145,618 or in the British Patent No. 1,390,649. They can be obtained in good yields by reacting, for example, 2 moles of fumaric acid or maleic acid, at a temperature of above 70° C., with at least one mole of an amidine of the formula III

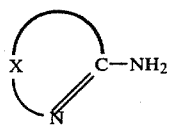

(III)

to give a compound of the formula IV

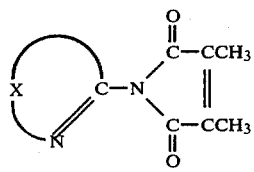

(IV), in which formulae the symbol X together with the grouping

forms the radical of a 5- or 6-membered, optionally further substituted, heterocycle which can contain further hetero atoms, especially S, N or O.

The ring, which is formed in the compound of the formulae III and IV by X together with the grouping

, can already correspond to the radical R of the formulae I and II if compounds in which R represents a nitrogen-containing unsaturated 5-6-membered heterocycle are desired. If compounds having another radical R are desired, the compound of the formula IV can be hydrolysed an an acid medium to give 2,3-dimethyl-maleic acid anhydride, which can then be easily condensed with a primary amine of the formula V

 (V), wherein R has the meaning given under the formula I, in the melt or in an inert solvent, directly to the imide of the formula II.

The following Examples illustrate the processes for producing arbitrarily selected active substances of the formula I. Other active substances, produced in a corresponding manner, are listed in the Tables which follow. Temperature values are in every case in degrees Centigrade.

EXAMPLE 1

N-(2'-Pyridyl)-3,4-dimethyl-2-hydroxy-5-oxo-2,5-dihydropyrrole 20.2 g (0.1 mole) of N-(2-pyridyl)-dimethyl-maleimide is suspended in 200 ml of methanol and the suspension is cooled. There is then introduced portionwise at an internal temperature of 0°–5° in the course of 2 hours, with stirring, 1.9 g (0.05 mole) of $NaBH_4$. The reaction is finished after one hour with stirring at room temperature. An addition of 100 ml of $H_2O$ is made with cooling, and the methanol is subsequently distilled off in a rotary evaporator at a bath temperature of 50°. The product commences to crystallise during distillation, and the crystals are finally filtered off under suction and afterwashed with 50 ml of $H_2O$.

Yield: 18.5 g, m.p. 101°–102°; 91% of theory (compound No. 1, in Table II).

EXAMPLE 2

N-(3'-methylphenyl)-3,4-dimethyl-2-hydroxy-5-oxo-2,5-dihydropyrrole 26.2 g (0.2 mole) of dimethylmaleic acid anhydride is put together with 21.4 g (0.2 mole) of 3-toluidine, and the whole is heated to 130°, with water distilling off at this temperature. After about 1 hour, the cooled reaction mixture is dissolved in methanol and the solution is cooled to 0°. The product crystallises during cooling, and is filtered off and dried to give light-yellow crystals having a melting point of 83°–84°. The yield is 35 g (81.4% of theory).

To 20 g (0.93 mole) of the resulting N-(3-methylphenyl)-dimethyl-maleimide in 180 ml of methanol is added at 20° 7.2 g (0.185 mole) of sodium borohydride in portions so small that the temperature does not exceed 40°. An intense evolution of gas is observed. The reaction mixture is initially a clear colourless solution, but soon becomes a white suspension, which is poured after one hour into water. The white substance which has precipitated out is filtered off, washed well with methanol and dried under reduced pressure to obtain 18.6 g of white crystals (92.1% of theory), which melt at 170°–172° (compound No. 9, Table I).

EXAMPLE 3

N-(3',4'-Dichlorophenyl)-3,4-dimethyl-2-hydroxy-5-oxo-2,5-dihydropyrrole

In a manner analogous to that of Example 2, 26.2 g (0.2 mole) of dimethylmaleic acid anhydride and 32.6 g (0.2 mole) of 3,4-dichloroaniline are condensed to give N-(3,4-dichlorophenyl)-dimethyl-maleimide, which is then dissolved in 300 ml of methanol. To this solution is slowly added in portions, with stirring, 10.8 g of sodium borohydride. After the addition is complete and the generation of gas has subsided, the reaction mixture is poured into ice water. The white precipitate is filtered off, washed with methanol and dried. There is obtained 49.3 g (84% of theory) of the above product in the form of colourless crystalline powder, m.p. 188°.

EXAMPLE 4

N-(5'-Methylpyrid-2'-yl)-3,4-dimethyl-2-hydroxy-5-oxo-2,5-dihydropyrrole 21.6 g (0.1 mole) of N-(5'-methylpyrid-2'-yl)-dimethylmaleimide is suspended in 200 ml of toluene, and the suspension with 1 g of an $RuCl_2 [P(C_6H_5)_3]_2$ catalyst is placed into a hydrogenating autoclave and hydrogenated at 100°–110° under 30–50 bars. The theoretical amount of hydrogen has been absorbed after 2–5 hours. The reaction mixture is separated from the catalyst by filtration, and the filtrate is evaporated to dryness under reduced pressure. The residue is recrystallised from ethyl acetate to yield 16.4 g (75% of theory) of the above compound in the form of colourless crystals, m.p. 118°–119°.

EXAMPLE 5

N-(3',4'-dichlorophenyl)-3,4-dimethyl-2-acetoxy-5-oxo-2,5-dihydropyrrole 27.2 g of N-(3',4'-dichlorophenyl)-3,4-dimethyl-2-hydroxy-5-oxo-2,5-dihydropyrrole (see Example 3) is refluxed together with 20.7 g of $K_2CO_3$ in 150 ml of methyl ethyl ketone. After cooling, there is added dropwise 8.2 g of acetyl chloride, with the temperature of the reaction mixture rising from 15° to 35°. The reaction mixture is filtered after 24 hours, and the filtrate is concentrated by evaporation. The residue is recrystallised from methanol to give 23.9 g (76% of theory) of the above product in the form of colourless crystals, m.p. 109°–110°.

EXAMPLE 6

N-(3',4'-Dichlorophenyl)-3,4-dimethyl-2-chloro-5-oxo-2,5-dihydropyrrole 27.2 g of N-(3',4'-dichlorophenyl)-3,4-dimethyl-2-hydroxy-5-oxo-2,5-dihydropyrrole (see Example 3) is added to 25 ml of thionyl chloride, with an intense evolution of gas occurring. After being stirred for one hour at 50°, the mixture is concentrated by evaporation in vacuo. The solid residue is triturated with petroleum ether to obtain 27.4 g (95% of theory) of the above compound in the form of light-yellow crystals, m.p. 95°–96°.

EXAMPLE 7

N-(3',4'-Dichlorophenyl)-3,4-dimethyl-2-fluoro-5-oxo-2,5-dihydropyrrole 23.2 g N-(3,4-dichlorophenyl)-3,4-dimethyl-2-hydroxy-5-oxo-2,5-dihydropyrrole (see Example 3) is refluxed together with 11.6 g of potassium fluoride and 0.3 g of 18-crown-6 (cyclic polyethylene ether) in 50 ml of acetonitrile for 14 hours. After cooling, undissolved constituents are filtered off, and the filtrate is concentrated by evaporation. The residue is recrystallised from methanol to yield 8 g (35% of theory) of the above product in the form of colourless crystals, m.p. 102°–103°.

EXAMPLE 8

N-(3',4'-Dichlorophenyl)-3,4-dimethyl-2-methyl-carbamoyloxy-5-oxo-2,5-dihydropyrrole 16.3 g of N-(3',4'-dichlorophenyl)-3,4-dimethyl-2-hydroxy-5-oxo-2,5-dihydropyrrole (see Example 3) is put together with 2 drops of triethylamine in 10 ml of glyme (ethylene glycol dimethyl ether), and 3.8 g of methylisocyanate is then added. After 24 hours, the reaction solution is filtered with a filtering auxiliary (Hyflo ®) and the filtrate is concentrated by evaporation to leave an oil, which is crystallised in methanol. In this manner is obtained 15 g (76% of theory) of the above product in the form of yellowish crystals, m.p. 141°–142°.

EXAMPLE 9

N-(5'-Methyl-pyrid-2'-yl)-3,4-dimethyl-2-acetoacetoxy-5-oxo-2,5-dihydropyrrole 15.3 g of N-(5'-methyl-pyrid-2'-yl-3,4-dimethyl-2-hydroxy-5-oxo-2,5-dihydropyrrole (see Example 4) and 5.9 g of diketene together with 20 ml of benzene are maintained for 5 hours at 50°. A further 3 g of diketene is then added and the reaction mixture is held at 50° for 4 hours. It is then concentrated by evaporation, and the residue is crystallised from acetonitrile to obtain 14.5 g (68% of theory) of the above product as colourless crystals, m.p. 112°–115°.

Table I

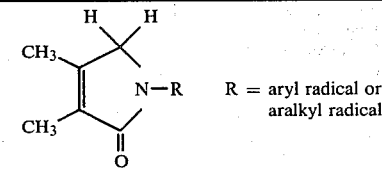

R = aryl radical or aralkyl radical

| Compound No. | R | A | Melting point |
|---|---|---|---|
| 1 | phenyl | OH | 129° |
| 2 | 3,4-dichlorophenyl | OH | 188° |
| 3 | 3,5-dichlorophenyl | OH | 188° |
| 4 | 4-chloro-3-trifluoromethylphenyl | OH | 160° |
| 5 | 4-fluorophenyl | OH | 168° |
| 6 | 2,6-dimethylphenyl | OH | 169° |
| 7 | 4-methylphenyl | OH | 193°–194° |
| 8 | 2-nitrophenyl | OH | 147° |
| 9 | 3-methylphenyl | OH | 170°–172° |
| 10 | 4-phenoxyphenyl | OH | 165°–167° |
| 11 | diphenyl | OH | 218°–220° |
| 12 | 3-chloro-4-methylphenyl | OH | 207°–208° |
| 13 | 3,4-dimethylphenyl | OH | 166°–168° |
| 14 | 4-dimethylaminophenyl | OH | 200°–202° |
| 15 | 4-bromophenyl | OH | 178°–179° |
| 16 | 4-chlorophenyl | OH | 178°–180° |
| 17 | 3-methoxyphenyl | OH | 137°–138° |
| 18 | 4-benzoylphenyl | OH | 146°–150° |
| 19 | 4-trifluoromethylphenyl | OH | 201°–202° |
| 20 | 4-methoxyphenyl | OH | 148°–149° |
| 21 | 4-methyl-3-nitrophenyl | OH | 195°–196° |
| 22 | 3-chloro-4-methoxyphenyl | OH | 171°–172° |
| 23 | 4-acetamidophenyl | OH | 268°–269° |
| 24 | 4-chloro-2-methylphenyl | OH | 154°–155° |
| 25 | 2-flourophenyl | OH | 124°–126° |
| 26 | 3-carboxyl-4-chlorophenyl | OH | 270° decomp. |
| 27 | 2-hydroxyphenyl | OH | 148° |
| 28 | 4-hydroxyphenyl | OH | 169° |
| 29 | 3,5-bis-(trifluoromethyl)phenyl | OH | 152°–154° |
| 30 | 3-trifluoromethylphenyl | OH | 192°–193° |
| 31 | 3-chlorophenyl | OH | 174°–175° |
| 32 | 3-bromophenyl | OH | 182°–183° |
| 33 | 3-hydroxyphenyl | OH | 223°–224° |
| 34 | 3-nitrophenyl | OH | 182°–183° |
| 35 | 3-methylthiophenyl | OH | 145°–146° |
| 36 | 3-methylcarbamoyloxyphenyl | OH | 167 zers |
| 37 | 3-mercaptophenyl | OH | 103°–105° |
| 38 | 3-carboxyphenyl | OH | 215° decomp. |
| 39 | 3-ethylphenyl | OH | 132°–133° |
| 40 | 3-sulphamoylphenyl | OH | 146°–147° |

Table I-continued $$\begin{array}{c} CH_3 \\ \diagdown \\ \phantom{CH_3}C=C \\ CH_3 \diagup \phantom{=} \diagdown \\ \phantom{CH_3=}C-N-R \\ \phantom{CH_3==}\| \\ \phantom{CH_3==}O \end{array}$$ R = aryl radical or aralkyl radical

| Compound No. | R | A | Melting point |
|---|---|---|---|
| 41 | 4-nitrophenyl | OH | 241° decomp. |
| 42 | 3-t.butylcarbamoyl-oxyphenyl | OH | 173°–175° |
| 43 | 3-aminophenyl | OH | 149°–150° |
| 44 | benzyl | OH | 102° |
| 45 | 2-chlorobenzyl | OH | 170° |
| 46 | 3-chlorobenzyl | OH | 120° |
| 47 | 4-chlorobenzyl | OH | 115° |
| 48 | 3-amino-4-methylphenyl | OH | 172°–173° |
| 49 | α-phenylethyl | OH | 100° |
| 50 | 4-methylbenzyl | OH | 127° |
| 51 | 4-methoxy-3-trifluoromethylphenyl | OH | 186°–188° |
| 52 | 3-chloro-4-trifluoromethylphenyl | OH | 187°–189° |
| 53 | 4-(4'-chlorophenoxy)-phenyl | OH | 167°–168° |
| 54 | 4-ethoxy-3-trifluoromethylphenyl | OH | 173°–175° |
| 55 | 3-chloro-4-fluorophenyl | OH | 188°–190° |
| 56 | 4-fluoro-3-trifluoromethylphenyl | OH | 175°–177° |
| 57 | 3,4-dimethoxyphenyl | OH | 158°–159° |
| 58 | 3,4-dichlorophenyl | Cl | 95°–96° |
| 59 | 3,4-dichlorophenyl | F | 102°–103° |
| 60 | 3,4-dichlorophenyl | OCOCH$_3$ | 109°–110° |
| 61 | 3,4-dichlorophenyl | OCONHCH$_3$ | 141°–142° |
| 62 | 3-methylphenyl | OCOCH$_3$ | oil |
| 63 | 3-methylphenyl | OCONHCH$_3$ | 135°–137° |
| 64 | 3-methylphenyl | OCOCH=CH$_2$ | oil |
| 65 | 3-methylphenyl | OCOCH=CHCH$_3$ | oil |
| 66 | 3-methylphenyl | OCOCH$_2$COCH$_3$ | 82°–83° |
| 67 | 3-nitrophenyl | OCOCH$_3$ | 123°–125° |
| 68 | 4-nitrophenyl | OCONHCH$_3$ | 174°–175° |
| 69 | 3-methylthiophenyl | OCONHCH$_3$ | 94°–95° |
| 70 | 3-chloro-4-trifluoromethylphenyl | OCOCH$_2$COCH$_3$ | 108°–109° |

Table II

R = heterocyclic radical

| Compound No. | R | A | Melting point |
|---|---|---|---|
| 1 | 2-pyridyl | OH | 101°–102° |
| 2 | 2-thiazolyl | OH | 123° |
| 3 | 3-hydroxy-2-pyridyl | OH | 111° |
| 4 | 5-chloro-2-pyridyl | OH | 139° |
| 5 | 5-methyl-2-pyridyl | OH | 122° |
| 6 | 4,6-dimethyl-2-pyrimidyl | OH | 181° |
| 7 | 3-methyl-2-pyridyl | OH | 188° |
| 8 | 4-pyridyl | OH | 214° |
| 9 | 5-nitro-2-pyridyl | OH | 214° |
| 10 | 3-pyridyl | OH | 180° |
| 11 | 6-methyl-2-pyridyl | OH | 115° |
| 12 | 4-methyl-2-pyridyl | OH | 112° |
| 13 | 5-methylthio-1,3,4-thiadiazol-2-yl | OH | 201°–02° |
| 14 | 5-trifluoromethyl-1,3,4-thiadiazol-2-yl | OH | 173°–14° |
| 15 | 4-t.butyl-thiazol-2-yl | OH | 94°–95° |
| 16 | 4-methyl-thiazol-2-yl | OH | 168°–169° |
| 17 | 1,3-dimethyl-pyridazol-6-yl | OH | 191°–192° |
| 18 | 6-hydroxy-pyrazin-3-yl | OH | 230°–233° |
| 19 | 2-pyridyl HCl | OH | 205° decomp. |
| 20 | 2-pyrazine | OH | 128°–129° |

Table II-continued

R = heterocyclic radical

| Compound No. | R | A | Melting point |
|---|---|---|---|
| 21 | 2,6-dimethyl-pyrimidin-3-yl | OH | 178°–179° |
| 22 | 6-acetamidopyrid-2-yl | OH | 199° |
| 23 | (3'-pyridyl)-methyl | OH | 110° |
| 24 | (4'-pyridyl)-methyl | OH | 143° |
| 25 | 5-acetamido-pyrid-2-yl | OH | 286° |
| 26 | 4,6-dimethyl-pyrid-2-yl | OH | 116° |
| 27 | 5-methyl-oxal-2-yl | OH | 167°–168° |
| 28 | 3-methyl-(1'2'4'-thiadiazol)-5-yl | OH | 173°–175° |
| 29 | 4-amino-5-cyano-6-piperidyl-pyrid-2'-yl | OH | >280° decomp. |
| 30 | 6-amino-pyrid-2-yl . HCl | OH | 263° |
| 31 | 2-(indol-3'-yl-ethyl | OH | 175° |
| 32 | 3-hydroxy-5-chlor-pyrid-2-yl | OH | 166° |
| 33 | 3-methoxy-pyrid-2-yl | OH | 159° |
| 34 | 4-ethyl-pyrid-2-yl | OH | 59° |
| 35 | 4-tert.butyl-pyrid-2-yl | OH | 87° |
| 36 | 2-pyridyl | OCONHCH$_3$ | 140°–141° |
| 37 | 2-pyridyl | OCOCH$_2$COCH$_3$ | 114°–115° |
| 38 | 2-pyridyl | OCDCH=CH$_2$CH$_3$ | 106°–107° |
| 39 | 2-pyridyl | OCOC(CH$_3$)=CH$_2$ | 143°–145° |
| 40 | 2-pyridyl | OC$_2$H$_4$Cl | 125°–126° |
| 41 | 2-pyridyl | OCOOC$_2$H$_5$ | 63°–65° |
| 42 | 2-pyridyl | OCO-cyclopropyl | 130°–131° |
| 43 | 5-methyl-pyrid-2-yl | OCOCH$_2$COCH$_3$ | 130°–131° |
| 44 | 5-methyl-pyrid-2-yl | OCOCH$_3$ | 109°–110° |
| 45 | 5-methyl-pyrid-2-yl | OCOCH$_2$Cl | 113°–115° |
| 46 | 5-methyl-pyrid-2-yl | OCOOC$_2$H$_5$ | 117°–119° |
| 47 | 5-methyl-pyrid-2-yl | OCO-cyclopropyl | 136°–137° |
| 48 | 5-methyl-pyrid-2-yl | OCONHCH$_3$ | 153°–154° |
| 49 | 5-methyl-pyrid-2-yl | OCON(CH$_3$)$_2$ | 147°–148° |
| 50 | 5-methyl-pyrid-2-yl | OCOCH=CHCH$_3$ | 95°–96° |
| 51 | 5-methyl-pyrid-2-yl | OCOSC$_2$H$_5$ | 91°–92° |
| 52 | 5-methyl-pyrid-2-yl | OCOtert.C$_4$H$_9$ | 114°–115° |
| 53 | 5-methyl-pyrid-2-yl | OCO-phenyl | 119°–120° |
| 54 | 5-methyl-pyrid-2-yl | OCOisoC$_3$H$_7$ | 87°–88° |
| 55 | 5-methyl-pyrid-2-yl . HCl | Cl | 177°–178° decomp. |
| 56 | 5-methyl-pyrid-2-yl | OCOC(CH$_3$)$_2$-nC$_3$H$_7$ | 79°–80° |
| 57 | 4-t-butyl-thiazol-2-yl | OCONHCH$_3$ | 146°–147° |

The novel 3,4-dimethyl-2-hydroxy-5-oxo-2,5-dihydropyrrole compounds of the formula I have a versatile spectrum of activity, and are therefore excellently suitable for combating plant and animal pests, or for regulating plant growth. The effectiveness was determined by the tests described in the following Examples.

EXAMPLE 10

Herbicidal action with application of the active substances before emergence (pre-emergence) of the plants Immediately after sowing of the test plants, the surface of the soil is treated with an aqueous suspension, obtained from 25% wettable powders, of the active substances. The amount applied is chosen to be equivalent to 16 kg and 4 kg of active substance per hectare. The seed trays are kept in a greenhouse at 22°–25° C. with 50–70% relative humidity.

The following are used as test plants:

*Avena sativa, Sinapis alba*
*Setaria italica, Stellaria media*

The test is evaluated 20 days after application of the active substances.

The evaluation is made on the basis of the following scale of values from 1 to 9:

1 = plants dead,
2–4 = intermediate stages of damage (over 50% irreversible damage),
5–8 = intermediate stages of damage (below 50% irreversible damage),
9 = plants undamaged (control).

EXAMPLE 11

Herbicidal action with application of the active substances after emergence (post-emergence) of the plants The test plants are treated in the 2–4-leaf stage with aqueous suspensions (obtained from 25% emulsion concentrates) of the active substances. The amount applied corresponds to 4 kg of active substance per hectare.

The following are used as test plants:

*Avena sativa, Sinapis alba*
*Setaria italica, Stellaria media*
*Lolium perenne, Gossypium hirsutum*
*Solanum lycopersianum, Phaseolus vulgares*

The plants are kept after the treatment for 14 days in a greenhouse under normal conditions, and the evaluation is then made on the basis of the scale of values from 1 to 9 as in Example 10.

EXAMPLE 12

Growth reduction in the case of grasses (Application after emergence of the plants (post-emergence))

Seeds of the grass varieties *Lolium perenne, Poa pratensis, Festuca ovina* and *Dactylis glomerata* are sown in plastic dishes containing a soil/peat/sand mixture. After 3 and 4 weeks, the emerged grasses are cut back to 4 cm above the soil, and 2 days after the second cutting are sprayed with aqueous spray liquors containing the active substance. The amount of active substance is equivalent to 5 kg of active substance per hectare. Fourteen days after application, the growth of the grasses is evaluated according to the following linear scale of ratings:

1 = severe reduction, no growth after application;
9 = no reduction, growth as in the case of the control specimens.

EXAMPLE 13

Action against *Fusarium oxysporum* on *Solanum lycopersicum*

(a) Action after soil treatment

Tomato plants are damaged at the roots after cultivation for 3 weeks and are then infested with a spore suspension of the wilt pathogen. After 24 hours, a spray liquor produced from wettable powder of the active substance is poured around the infested tomato plants (60 ppm relative to the final liquor volume). After an incubation period of 14 days in a greenhouse at about 22° C., the degree of wilt of the plants is assessed.

(b) Action after leaf treatment

After 3-weeks' cultivation, the roots of tomato plants are damaged and the plants infested with a spore suspension of the wilt pathogen. After 24 hours, the plants are sprayed with a spray liquor (0.18% of active substance) prepared from wettable powder of the active substance. After an incubation period of 14 days in a greenhouse at about 22° C., the degree of wilt of the infested tomato plants is determined.

EXAMPLE 14

Action against red spider mites

Bush bean plants (*Phaseolus vulgaris*) are infested in the two-leaf stage, 12 hours before treatment with the active substance, with red spider mites by placing onto the plants infested pieces of leaf from a culture, so that after this period of time (12 hours) there is present on the plants a population in all stages of development. The plants are then sprayed with the emulsified active substance using a chromatography sprayer until a uniform coating of droplets is formed on the surface of the leaves. An evaluation is made after 2 and 7 days: the parts of the plants are examined under a stereomicroscope in order to calculate the mortality percentages.

EXAMPLE 15

Growth reduction in soya bean crops

Smallish plots sown with soya bean plants are sprayed in the blossom period with an aqueous preparation of one of the compounds according to the invention, and this treatment is repeated 5 times in each test. At the same time, control plots are left untreated. At the point of time for harvesting, the mean height of growth of the plants and the yield is determined for each plot.

EXAMPLE 16

Dessication and defoliation of cotton plants

Cotton plants of the variety "Delta Pine" are grown in a greenhouse, and are sprayed after blossoming using aqueous suspensions of the given active substances. The concentration of active substance in the spray liquor is 1%, and 20 ml of liquor is sprayed on. Plants treated with water only are used as control plants. Fourteen days after application, the plants are evaluated with respect to defoliation and dessication. The following rating system is used for this purpose:

rating 9 = 0 to 11% defoliation and dessication,
rating 8 = 12 to 22% defoliation and dessication,
rating 7 = 23 to 33% defoliation and dessication, and
rating 1 = 89 to 100% defoliation and dessication.

The compositions according to the invention are produced in a manner known per se by the intimate mixing and/or grinding of active substances of the general formula I with suitable carriers, optionally with the addition of dispersing agents or solvents which are inert to the active substances. The active substances can be obtained and used in the following forms:

solid preparations: dusts, scattering agents, granules (coated granules, impregnated granules and homogeneous granules;

active-substance concentrates dispersible in water: wettable powders, pastes and emulsions;

liquid preparations: solutions.

The solid preparations (dusts, scattering agents and granules) are produced by mixing the active substances with solid carriers. These can be, e.g., kaolin, talcum, bole, loess, chalk, limestone, ground limestone, Atta-clay, dolomite, diatomaceous earth, precipitated silicic acid, alkaline-earth silicates, sodium and potassium aluminium silicates (feldspars and mica), calcium and magnesium sulphates, magnesium oxide, ground synthetic materials, fertilisers such as ammonium sulphate, ammonium phosphate, ammonium nitrate, urea, ground vegetable products such as bran, bark dust, sawdust, ground nutshells, cellulose powder, residues of plant extractions, active charcoal, etc., alone or in admixture with each other.

The particle size of the carriers is for dusts advantageously up to about 0.1 mm; for scattering agents about 0.075 to 0.2 mm; and for granules 0.2 mm or coarser.

The concentration of active substance in the solid preparations is 0.5 to 80%.

It is possible to add to these mixtures also additives stabilising the active substance, and/or nonionic, anion-active and cation-active substances which improve, e.g., the adhesiveness of the active substances on plants and parts of plants (adhesives and agglutinants), and/or ensure better wettability (wetting agents) and also dispersibility (dispersing agents). Suitable adhesives are, for example, olein/lime mixtures, cellulose derivatives (methyl cellulose, carboxymethyl cellulose), hydroxyethylene glycol ethers or monoalkyl and dialkyl phenols having 5 to 15 ethylene oxide radicals per molecule and 8 to 9 carbon atoms in the alkyl radical, ligninsulphonic acid, the alkali metal salts and alkaline-earth metal salts thereof, polyethylene glycol ethers (carbowaxes), fatty alcohol polyglycol ethers having 5 to 20 ethylene oxide radicals per molecule and 8 to 18 carbon atoms in the fatty alcohol moiety, condensation products of ethylene oxide, propylene oxide, polyvinylpyrrolidones, polyvinyl alcohols, condensation products of urea and formaldehyde, and also latex products.

Water-dispersible concentrates of active substances, e.g. wettable powders, pastes and emulsion concentrates, are agents which can be diluted with water to give the desired concentration. They consist of active substance, carrier, optionally additives stabilising the active substance, surface-active substances, and antifoaming agents and, optionally, solvents. The concentration of active substance in these preparations is 5–80%.

The wettable powders and pastes are obtained by mixing and grinding the active substances with dispersing agents and pulverulent carriers, in suitable devices, until homogeneity is obtained. Suitable carriers are, e.g., those previously mentioned in the case of solid preparations. It is advantageous in some cases to use mixtures of different carriers. As dispersing agents it is possible to use, e.g.: condensation products of sulphonated naphthalene and sulphonated naphthalene derivatives with formaldehyde, condensation products of naphthalene or of naphthalenesulphonic acids with phenol and formaldehyde, and also alkali metal salts, ammonium salts and alkaline-earth metal salts of ligninsulphonic acid, also alkylarylsulphonates, alkali metal salts and alkaline-earth metal salts of dibutyl-naphthalenesulphonic acid, fatty alcohol sulphates such as salts of sulphated hexadecanols, heptadecanols, octadecanols, and salts of sulphated fatty alcohol glycol ethers, the sodium salt of oleyl methyl tauride, ditertiary acetylene glycols, dialkyl dilauryl ammonium chloride, and fatty acid alkali-metal and alkaline-earth-metal salts.

Suitable antifoaming agents are, for example, silicones.

The active substances are mixed, ground, sieved and strained with the above-mentioned additives until the solid constituent in the case of wettable powders has a particle size not exceeding 0.02 to 0.04 mm, and in the case of pastes not exceeding 0.03 mm. For the preparation of emulsion concentrates and pastes, dispersing agents are used such as those mentioned in the preceding paragraphs, organic solvents and water. Suitable solvents are, e.g., alcohols, benzene, xylenes, toluene, dimethylsulphoxide, N,N-dialkylated amides, N-oxides of amines, especially trialkylamines, and mineral oil fractions boiling in the range of 120° to 350° C. The solvents must be practically odourless, nonphytotoxic, inert to the active substances and not readily combustible.

Furthermore, the compositions according to the invention can be used in the form of solutions. For this purpose, the active substance, or several active substances, of the general formula I is (or are) dissolved in suitable organic solvents, solvent mixtures, water, or mixtures of organic solvents with water. As organic solvents, it is possible to use aliphatic and aromatic hydrocarbons, their chlorinated derivatives, alkylnaphthalenes, mineral oils on their own or in admixture with each other. The solutions should contain the active substances at a concentration of 1 to 20%.

These solutions can be applied either by means of a propellent gas (as spray), or by means of special sprayers (as aerosol).

Other biocidal active substances or agents can be mixed with the described compositions according to the invention. For the broadening of their sphere of action, the novel compositions can for example contain, in addition to the stated compounds of the general formula I, other herbicides, and also fungicides, bactericides, fungistatics, bacteriostatics or nematocides. The compositions according to the invention can also contain fertilisers, trace elements, etc.

Preparations of the novel active substances of the general formula I are described in the following. Parts are given as parts by weight.

Wettable powders

The following constituents are used to produce (a) a 40%, (b) and (c) a 25%, and (d) a 10% wettable powder:

(a)

40 parts of active substance,
5 parts of sodium lignin sulphonate,
1 part of sodium dibutyl-naphthalene sulphonate,
54 parts of silicic acid;

(b)

25 parts of active substance, 4.5 parts of calcium lignin sulphonate,
1.9 parts of Champagne chalk/hydroxyethyl cellulose mixture (1:1),
1.5 parts of sodium dibutyl-naphthalene sulphonate,
19.5 parts of silicic acid,
19.5 parts of Champagne chalk,
28.1 parts of kaolin;

(c)

25 parts of active substance,
2.5 parts of isooctylphenoxy-polyoxyethylene-ethanol,
1.7 parts of Champagne chalk/hydroxyethyl cellulose mixture (1:1),
8.3 parts of sodium aluminum silicate,
16.5 parts of kieselguhr,
46 parts of kaolin;

(d)

10 parts of active substance,
3 parts of a mixture of the sodium salts of saturated fatty alcohol sulphates,
5 parts of naphthalenesulphonic acid/formaldehyde condensate,
82 parts of kaolin.

The active substances are intimately mixed in suitable mixers with the additives, and the mixture is then ground in the appropriate mills and rollers to give wettable powders which can be diluted with water to obtain suspensions of the desired concentration.

Emulsifiable concentrates

The following substances are used to produce (a) a 10% and (b) a 25% emulsifiable concentrate:

(a)

10 parts of active substance,
3.4 parts of epoxidised vegetable oil,
3.4 parts of a combination emulsifier consisting of fatty alcohol polyglycol ether and alkylarylsulphonate calcium salt,
40 parts of dimethylformamide,
43.2 parts of xylene; and (b)

25 parts of active substance,
2.5 parts of epoxidised vegetable oil,
10 parts of an alkylarylsulphonate/fatty alcohol polyglycol ether mixture,
5 parts of dimethylformamide,
57.5 parts of xylene.

Emulsions of the concentration desired can be prepared from these concentrates by dilution with water.

We claim:

1. A 3,4-dimethyl-2-hydroxy-5-oxo-2,5-dihydropyrrole compound of the formula I

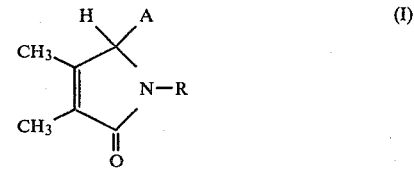

wherein

A represents the hydroxyl group, a halogen atom or an O-acyl radical, wherein said acyl portion is derived from ($C_1$–$C_{12}$ alkyl) carboxylic acid, ($C_1$–$C_{12}$ alkyl) carboxylic acid substituted by halogen or having the alkyl group interrupted by oxygen or a -CO- group, ($C_2$–$C_{12}$ alkenyl) carboxylic acid, ($C_3$–$C_6$ cycloalkyl) carboxylic acid, ($C_1$–$C_4$ alkoxy-) or ($C_1$–$C_4$ alkylthio-) carboxylic acid, mono- or di-substituted ($C_1$–$C_4$ alkyl) carbamoyloxy acid, or benzoic acid; and R represents phenyl, naphthyl, benzyl or phenethyl, or phenyl, naphthyl, benzyl or phenethyl substituted by halogen, $C_1$–$C_4$ alkyl, $C_1$–$C_4$ alkoxy, $C_1$–$C_4$ alkylthio, $C_2$–$C_4$ alkenyloxy, $C_1$–$C_4$ haloalkyl, $C_2$–$C_4$ haloalkenyl, $C_3$–$C_4$ alkynyl, $C_3$–$C_4$ alkynyloxy, phenyl, phenoxy, benzyloxy, nitro, cyano, hydroxyl, mercapto, carboxyl, benzoyl, acetamido, $C_1$–$C_4$ alkylcarbamoyloxy, amino mono- or di-substituted ($C_1$–$C_4$ alkyl) amino, sulphinyl, sulphonyl or sulphamoyl.

2. The compounds of the formula I, claim 1, wherein A represents the OH group.

3. The compound of the formula I, claim 1, wherein R represents phenyl or phenyl substituted by the indicated substituents.

4. Composition for combatting plant and animal pests, which composition contains as active substance a pesticidally effective amount of a 3,4-dimethyl-2-hydroxy-5-oxo-2,5-dihydro-pyrrole compound of the formula I, claim 1, together with a suitable carrier therefor.

5. A method for combatting plant and animal pests which comprises applying to the locus thereof a pesticidally effective amount of a 3,4-dimethyl-2-hydroxy-5-oxo-2,5-dihydro-pyrrole compound of the formula I, claim 1.

* * * * *